United States Patent [19]

Bozich, Jr.

[11] Patent Number: 5,360,854

[45] Date of Patent: Nov. 1, 1994

[54] HOT MELT PRESSURE SENSITIVE ADHESIVE COMPOSITION AND APPLICATIONS

[75] Inventor: Frank A. Bozich, Jr., Elmhurst, Ill.

[73] Assignee: Adhesive Technology, Inc., Itasca, Ill.

[21] Appl. No.: 63,364

[22] Filed: May 17, 1993

Related U.S. Application Data

[63] Continuation of Ser. No. 711,371, Jun. 3, 1991, abandoned, which is a continuation of Ser. No. 518,102, May 1, 1990, abandoned, which is a continuation-in-part of Ser. No. 279,837, Dec. 5, 1988, abandoned.

[51] Int. Cl.$^5$ .............................. C08L 25/10
[52] U.S. Cl. ........................... 524/274; 524/271; 524/499; 524/505; 524/474
[58] Field of Search ............... 524/271, 274, 499, 505, 524/474

[56] References Cited

U.S. PATENT DOCUMENTS

| | | | |
|---|---|---|---|
| 3,239,478 | 3/1966 | Harlan, Jr. | 428/349 |
| 3,519,585 | 7/1970 | Miller | 524/271 |
| 3,681,190 | 8/1972 | Dahlquist | 428/356 |
| 3,783,072 | 11/1973 | Korpman | 156/244.23 |
| 3,787,531 | 1/1974 | Dahlquist et al. | 428/355 |
| 3,932,328 | 1/1976 | Korpman | 524/271 |
| 3,970,623 | 7/1976 | Feeney et al. | 524/274 |
| 4,088,346 | 7/1977 | Feeney | 524/575 |
| 4,136,071 | 1/1979 | Korpman | 524/274 |
| 4,288,567 | 9/1981 | Feeney et al. | 525/99 |
| 4,338,237 | 7/1982 | Ballard | 524/524 |
| 4,394,915 | 7/1983 | Nelson | 215/12 R |
| 4,578,302 | 3/1986 | Schmidt, Jr. et al. | 428/110 |
| 4,734,447 | 3/1988 | Hattori et al. | 524/271 |
| 4,835,200 | 5/1989 | St. Clair | 525/99 |
| 4,944,994 | 7/1990 | Flanagan | 428/343 |
| 5,057,571 | 10/1991 | Malcolm et al. | 524/505 |
| 5,093,406 | 3/1992 | Lossner et al. | 524/483 |

OTHER PUBLICATIONS

Abstract of Japanese Patent, 63-207875, Aug. 1988, Nakajima et al.
J. M. Tancrede, "Light Colored, Hydrocarbon Tackifiers For EVA and SBS Based Adhesive Systems", Presentation before the 1988 Tappi Polymers, Laminations and Coatings Conference, Atlanta, Georgia, Sep., 1988.
Ahner et al., "Unique Liquid Tackifiers For The Adhesives Industry", 1984.
Material Safety Data Sheet for ECR-140A.
Letter dated Sep. 12, 1985 from Exxon to H. B. Fuller Co.
Product Information Sheet, "Stereon 840A In Hot-Melt Pressure Sensitive Adhesives."

Primary Examiner—Paul R. Michl
Assistant Examiner—John J. Guarriello
Attorney, Agent, or Firm—Marshall, O'Toole, Gerstein, Murray & Borun

[57] ABSTRACT

The present invention is directed to a low viscosity, high tensile strength adhesive of the hot melt pressure sensitive type composition comprising:

(a) from about 15 to about 30% by weight of an A-B-A block or A-B-A-B-A-B- multi-block copolymer containing from about 35 to about 55 parts styrene per 100 parts polymer where polymer blocks A are styrene blocks and polymer blocks B are butadiene or hydrogenated butadiene;

(b) 70 to about 85% by weight to a composition tackifying resin; and (c) 0.1 to about 1.5% by weight of a stabilizer. Because the adhesive of the present invention has low viscosity and high tensile strength at both high and low temperatures, the adhesive formulation of the present invention is particularly well-suited to disposable diaper construction, hinge binding in books, PET bottle labeling, and attaching base cups to PET beverage bottles.

8 Claims, No Drawings

HOT MELT PRESSURE SENSITIVE ADHESIVE COMPOSITION AND APPLICATIONS

This is a continuation of application Ser. No. 07/711,371 filed Jun. 3, 1991, now abandoned which is a continuation of co-pending U.S. patent application Ser. No. 07/518,102, filed May 1, 1990, now abandoned, which is a continuation-in-part of U.S. patent application Ser. No. 07/279,837, filed on Dec. 5, 1988, now abandoned.

BACKGROUND OF THE INVENTION

A. FIELD OF THE INVENTION

The present invention relates to a hot melt pressure sensitive adhesive composition and to articles of manufacture incorporating the adhesive composition. The pressure sensitive adhesive of the present invention has the properties of low viscosity and high tensile strength without requiring viscosity adjusters, making it particularly useful for disposable diaper construction and hinge gluing in books. Further, it was discovered that the pressure sensitive adhesive of the present invention also has good high and low temperature performance making it useful for PET bottle labeling or mounting HDPE bases to PET beverage bottles.

B. Prior Art

Hot melt adhesive compositions are known throughout the disposables industry. However, it is equally well-known that a hot melt adhesive composition which is suited for bonding in one application may be completely unsuitable for other applications. For example, disposable diaper construction presents a unique set of problems to the adhesives formulator. The adhesive must possess a high degree of adhesion since it is applied in a series of very narrow lines or dots. Moreover, the adhesive must also possess sufficient adhesive and cohesive strength to provide high tensile strength bonds when subjected to stress so that the laminates used in the construction cannot be easily separated. Additionally, the adhesives must remain flexible and secure with age and not break down in a wet environment. Aesthetically, the adhesive should be white or clear in color.

U.S. Pat. No. 4,526,577 (Schmidt, Jr., et al.) discloses a multi-line construction disposable diaper employing a pressure sensitive hot melt adhesive whose composition requires at least four classes of components. The composition for the Schmidt adhesive comprises a block or multi-block copolymer; tackifying resins having high softening points (about 100°–120° C.); a plasticizing oil; optionally, a petroleum wax; and one or more stabilizers.

Pressure sensitive hot melt adhesive compositions have generally not been suited for performance in the disposable polyethyleneteriphthalic acid (PET) bottle industry, because these adhesive compositions lacked sufficient tensile strength at high and low temperatures. High and low temperature performance is important for maintaining the adherence of labels and the adherence of base cups on beverage bottles where the bottles are subject to repeated cycles of contraction and expansion caused by repeated cycles of refrigeration and room temperature warming.

U.S. Pat. No. 4,212,910 (Taylor et al.) discloses a hot melt adhesive composition suitable for PET bottle assemblies consisting essentially of four classes of components: (1) a block copolymer or a teleblock copolymer; (2) at least one tackifying resin; (3) at least one stabilizer; and (4) at least one wax or oil diluent.

SUMMARY OF THE INVENTION

An object of the present invention is to produce a hot melt pressure sensitive adhesive composition having increased strength and elasticity without sacrificing tackiness or viscosity.

The present invention is directed to a hot melt pressure sensitive "adhesive composition" having high tensile strength and elasticity comprising three classes of components:
- (a) 15 to 30% by weight of an A-B-A block or A-B-A-B- multi-block styrene butadiene copolymer wherein the styrene content of the copolymer was from 35–55 parts per 100;
- (b) 72 to 85% by weight of one or more compatible tackifying resins having a composite Ring and Ball ("R & B") softening point between about 25° to about 50° C.; and
- (c) 0.1 to 1.5% by weight of a stabilizer. Optionally, 0 –5% wax can be added to the adhesive composition, depending upon the utility.

Moreover, the present invention is also directed to a disposable diaper of the multi-line construction comprising at least one polyethylene or polypropylene substrate bonded to at least one tissue, or non-woven substrate using a hot melt pressure sensitive adhesive composition comprising:
- (a) 15 to 28% by weight of a A-B-A block or A-B-A-B-A-B- multi-block copolymer containing from about 35 to about 55 parts styrene per 100 parts polymer where polymer blocks A are styrene blocks and polymer blocks B are butadiene or hydrogenated butadiene:
- (b) 72 to 85% by weight of one or more tackifying resins having a composite Ring and Ball ("R & B") softening point between about 25° to about 50° C.; and
- (c) 0.1 –1.5% by weight of a stabilizer.

An especially preferred adhesive composition for use in the above-mentioned construction employs 20% by weight of a multi-block copolymer having 42–52 parts styrene per 100 parts of polymer.

Additionally, the present invention also encompasses a book wherein the book cover is attached to the edges of the bound signatures of the book employing the adhesive composition of the present invention.

Further, the present invention also encompasses a PET bottle wherein a label is affixed thereto by the adhesive Formulation of the present invention, or a PET beverage bottle wherein a HDPE base cup is affixed to the PET beverage bottle by the adhesive Formulation of the present invention.

DETAILED DESCRIPTION OF THE PREFERRED EMBODIMENT

The present invention is directed to a hot melt pressure sensitive adhesive composition ("adhesive composition") having low viscosity and high tensile strength and particularly preferred articles of manufacture employing the adhesive composition of the present invention.

Unlike the hot melt, pressure sensitive adhesive compositions in the prior art, which employ at least four or more classes of components, the adhesive composition of the present invention requires only three classes of components: (1) copolymer, (2) tackifying resin, and (3)

stabilizer. In particular, it was discovered that the conventional use of plasticizing oils and/or waxes, which do not contribute to tensile strength, have been completely eliminated from the adhesive composition of the present invention. Further, it was discovered that the viscosity of a hot melt adhesive composition could be lowered without sacrificing tensile strength if the conventionally employed combination of high softening point (>70° C.) terpene tackifiers and plasticizing oils were substituted for by one or more compatible tackifying resins having a composite Ring and Ball ("R & B") between about 25° C. to about 50° C. In addition, it was unexpectedly discovered that the resultant adhesive composition of the present invention has a relatively flat curve for viscosity versus temperature making it particularly well suited for applications where viscosity constraints are involved or for applications requiring both high and low temperature performance.

The adhesive composition of the present invention comprises:
  (a) 15–30% by weight of copolymer;
  (b) 70 to 85% by weight of one or more compatible tackifying resins having a composite Ring and Ball ("R & B") softening point between about 25° C. to about 50° C.; and
  (c) 0.1–1.5% by weight of a stabilizer.

The "copolymer" component of the present invention comprises A-B-C block or A-B-A-B-A-B multi-block copolymers wherein the "A" polymer blocks are non-elastomeric blocks and the "B" polymer blocks are elastomeric blocks. The "non-elastomeric blocks" make up 35–55 parts per 100 (by weight) of the copolymer, preferably 42–52 parts per 100 (by weight). Typically, these non-elastomeric blocks are monovinyl aromatic hydrocarbons of the benzene series such as styrene, vinyl toluene, vinyl xylene and ethyl vinyl benzene. Especially preferred is styrene. The "elastomeric polymer blocks" make up the balance of the copolymer. Preferably, this component is butadiene which may optionally be partially or completely hydrogenated as taught, for example, in U.S. Pat. No. 3,700,633. By selecting the appropriate conditions for hydrogenation, it is possible to selectively hydrogenate the elastomer without modifying the vinyl arene block polymer. Optionally, by selecting other conditions, hydrogenation of the entire polymer chain can be partially or substantially affected.

Preferably, the A-B-A block and A-B-A-B-A-B- multi-block copolymers used in the present invention employ polystyrene as the "A" block and polybutadiene as the "B" block. These copolymers may be prepared using the methods taught, for example, in U.S. Pat. Nos. 3,239,478; 3,427,269, and 3,932,327. Alternatively, many of these copolymers are commercially available from Enichem Americas under the trademarks Europrene SOLT 168 and SOLT 166 or from Shell (Oil) Chemical Company under the trademarks Kraton 1101, 1102, 1650, 1652, and 1657 respectively.

Most preferred for use in the present invention are the A-B-A-B-A-B- multi-block copolymers wherein the A block is polystyrene and the B block is polybutadiene. This copolymer is commercially available from Firestone under the trademark Steron 845A, having a molecular weight range from about 64,000 to about 98,000.

The "tackifying resin" component of the present invention comprises one or more compatible tackifying resins and has a composite R & B softening point of between about 25° C. and about 50° C, preferably between 30° C. and 45° C. By "composite R & B softening point" as used herein in relation to the tackifying resins is meant either the R & B softening point of the individual tackifier when only a single tackifier makes up the tackifying resin component, or the R & B softening point of the blended tackifiers when more than one tackifier makes up the tackifying resin component.

For purposes of the present invention, tackifying resins having a composite R & B softening point substantially below 25° C. result in an adhesive that is considered too soft to adhere at room temperature, whereas tackifying resins having an R & B softening point substantially above 50° C. result in an adhesive that is too brittle to adhere at room temperature.

The tackifying resin component of the present invention can be produced in one of two ways, either by blending two or more compatible tackifying resins or by selection of a single tackifying resin. For example, in blending tackifying resins, one or more tackifying resins that have a softening point greater than 50° C. is blended with a sufficient amount of one or more tackifying resins have a softening point below 25° C. (i.e., "liquid" resins) resins to obtain a composite resin having a composite R & B softening point ranging between about 25° C. to about 50° C. A number of tackifying resins having a R & B softening point greater than 70° C. are disclosed in U.S. Pat. No. 4,526,577 at Col. 3 which is herein incorporated by reference.

Alternatively, one or more tacking resins having softening points falling within the range of about 25° C. to about 50° C. may be blended together to provide a tackifying resin having a composite R & B softening point between about 25° C. and about 50° C. Various other combinations of tackifying resins can be envisioned and their combination is within the ordinary skill of those in the art. It is only necessary that the final tackifying resin component have a softening point ranging from about 25° C. to about 50° C.

It is also within the scope of this invention to employ a single tackifying resin as the tackifying resin component of the invention. As with the blends of tackifiers, the single tackifying resin should be compatible with the other ingredients and itself have an R & B softening point of between about 25° C. and about 50° C.

By varying the tackifying resin component of the present invention, it is possible to optimize performance (i.e., adhesion) or to strike a balance between performance and cost. To produce a high performance adhesive, such as taught in Example 1, the tackifying resin component is preferably composed of the following:

1. a "polyterpene resin/petroleum hydrocarbon resin" having a Ring and Ball softening point of about 10° C. and an average molecular weight of 450 daltons (commercially available from Goodyear Chemicals under the trademark Wingtack 10);
2. a 37 light colored hydrocarbon resin" having a Ring and Ball softening point from about 100° –110° C. (commercially available from Exxon Chemical Co. under the trademark Ecorez 149-A); and
3. a "synthetic petroleum hydrocarbon resin" having a Ring and Ball ("R & B") softening point of about 20° C., as determined by ASTM E-28, and a molecular weight range of 490–580 daltons (commercially available from Exxon Chemicals under the trademark Escorez 2520).

Preferably, the ratio by weight of the three resin components disclosed above is about 5:6:5 respectively.

In terms of weight percent relative to the total adhesive composition, the preferred weight range for the three resins comprising the tackifying resins composition is as follows:

1. polyterpene resin/petroleum hydrocarbon resins, range: 20 –30%;
2. high melt point hydrocarbon resin, range: 25 –35%;
3. synthetic petroleum hydrocarbon resins, 20 –28%.

Using the present invention, it is possible to provide a quality adhesive such as in Example 2 to provide a quality adhesive wherein a minimal amount of performance is sacrificed (Table 1), but significant economic advantage is gained. Notwithstanding the sacrifice in performance to gain economic advantage, the adhesive composition of Example 2 still out performs the prior art adhesive of the Schmidt '577 patent both in total elongation (19.96 in./5010% versus 9.8 in./2591%) and in peak tensile strength (4.43 lbs. versus 3.77 lbs.). Although relevant, the "tackiness" of the adhesive of Example 2, as measured by the Polyken Probe, is not as important as the total elongation and peak tensile strength. In particular, the tackiness of Example 2, which is 625 grams ("gms"), is more than adequate for use in disposable articles construction. Further, in the disposable articles construction, the glue is applied hot (i.e., as a flowable liquid) and then mated before it hardens. As a result, the hot glue flows into pores and/or inter-fiber spaces causing it to mechanically grab when it does harden.

Significant economic advantage can be obtained by employing a tackifying resin having an R & B softening point between about 55 ° C. and 65° C. It is our understanding that such a tackifying resin is very economical to formulate relative to the higher softening point resins, but that heretofore there has been no significant demand in any industry for such a resin. Any current demands are satisfied by blending the high and low softening point resins. Because the high softening point resins are more expensive to produce, blending them with low softening point resins results in a loss of economic advantage. A typical hot melt adhesive composition employing an aromatically modified C5 resin having a softening point between 55 ° C. and 65 ° C. is presented in Example 3.

In the present invention, the amount of high softening point tackifiers may also be decreased by decreasing the mono-vinyl-aromatic hydrocarbon (e.g., styrene) content of the A-B-A or the A-B-A-B-A-B- multi-block copolymer.

The stabilizers used in the present invention are of the antioxidant type. Generally, these antioxidants are members of the group comprising high molecular weight sterically hindered phenols, or sulfur- or phosphorus-substituted phenols. By "sterically hindered phenols" is meant those phenols with two isopropyl or preferable tertiary butyl groups ortho to the phenolic hydroxyl group. Representative sterically hindered phenols include:

1,3,5-trimethyl 2,4,6-tris (3,5-di-terbutyl-4-hydroxybenzyl)benzene; pentaerythrityl tetra-kis-3(3,5-di-tert-butyl-4-hydroxyphenyl)propionate; n-octadecyl-3(3,5-di-tert-butyl-4-hydroxyphenyl)-propionate; 4,4'-methylenebis (2,6-tert-butylphenol); 4,4'-thiobis (6-tert-butyl-o-cresol); 2,6-di-tertbutylphenol; 6-(4-hydroxyphenoxy)-2,4-bis(n-octylthio)-1,3,5-triazine; di-n-octadecyl 3,5-di-tert-butyl-4-hydroxybenzylphosphonate; 2-(n-octylthio)ethyl 3,5-di-tert-butyl-4-hydroxybenzoate; and sorbitol hexa[4-(3,5-di-tert-butyl-4-hydroxyphenyl)propionate].

The stabilizers of the present invention may include either one of the above-mentioned antioxidants alone or in combination with thiodipropionate esters and phosphates such as distearylthiopropionate. A suitable stabilizer is Irganox 1010 which is available from Ciba-Geigy.

Unexpectedly it was discovered that the composition "tackifying resin" component of the present invention may comprise a compatible resin mixture wherein only approximately 50% or less of the resin mixture need be one of the more expensive high softening point resins, such as a light colored hydrocarbon resin having a Ring and Ball (R&B) softening point from about 100°–110° C.

The use of the highly available petroleum derived low softening point ($\leq 20°$ C.) tackifying resins in the present invention is in marked contrast to the prior art's use of the high softening point (>70° C.) modified terpene resins, such as Zonatac 105, described in U.S. Pat. No. 4,526,577 (Schmidt et al.). Whereas, the terpene resins, which are preferred in the prior art, are natural by-products that are continuously subject to industry shortages and rationing, the present invention's ability to provide a superior adhesive using the liquid tackifying resins, which are less expensive and more commercially available petroleum derived resins, is of significant technical and commercial advantage over the prior art. Further, by using liquid tackifying resins, the adhesive composition of the present invention eliminates the need for viscosity adjusters, such as oils, which reduce the overall tensile strength of the adhesive composition by reducing adhesion contributing solids content.

As a result of having a low viscosity coupled with a high tensile strength, the adhesive composition of the present invention is ideally suited for applications requiring the high speed machine application of adhesive, such as in a series of lines (multi-line), dots (multi-dot), or in a spray pattern.

The low viscosity high tensile strength adhesives of the present invention are particularly well-suited for product applications where a porous material is bound to another porous or non-porous material. Particularly preferred product applications for the adhesive composition of the present invention are the following disposable items: disposable diapers, incontinent devices, and sanitary napkins (collectively, "disposable sanitary items") of the multi-line or spray construction type; disposable polyethyleneteriphthalic acid ("PET") bottles wherein the label is affixed with the adhesive composition of the present invention; and disposable PET beverage bottles wherein the high density polyethylene base ("HDPE") cups are affixed to the base of the PET bottles by the adhesive composition of the present invention.

By "multi-line" construction as used herein to describe disposable diaper construction is meant a construction technique in which adhesive is deposited in a multi-stripe or multi-dot pattern such that there are a large number of deposits, and the amount of each deposit is small. It is the high tensile strength and machinability of the adhesive composition of the present invention which make the adhesive composition particularly suited to this application. In particular, the size of each deposit requires that the adhesive have a high tensile strength, whereas the machinability provides the property necessary for the low cost application of adhesive to the disposable item. In a typical disposable diaper construction of the multi-line type, the adhesive composition is used to bond polyethylene ("PE") or polypropylene ("PP") substrates to tissue, non-wovens or other PE or PP substrates. See, for example, U.S. Pat. No. 4,526,577 (Schmidt et al.) which discusses the use of hot melt pressure sensitive adhesives in the "multi-line" technique and which is incorporated herein by reference.

The above description of multi-line construction for diapers is also applicable to the construction of incontinence devices and sanitary napkins, which similarly involve the adhesion of one or more woven and non-woven sheets. In the diaper, incontinence device and sanitary napkin (i.e., collectively, disposable sanitary item) industry, the spraying of the adhesive is expected to become increasingly preferred since the spray provides the disposable sanitary item manufacturers with a greater coverage based upon the same amount of adhesive. The hot melt adhesive of the present invention is particularly suited for spraying since it is substantially less viscous than the conventional hot melt adhesives used in multi-line construction, such as that disclosed in U.S. Pat. No. 4,526,577 (Schmidt et al.).

Unlike the hot melt pressure sensitive adhesive utilized for multi-line construction in the prior art, the adhesive composition of the present invention requires no plasticizing oil or waxes, thereby allowing for higher adhesion contributing solids and more tensile strength.

The adhesive composition of the present invention was unexpectedly discovered to have a relatively flat viscosity temperature curve, particularly when compared to the conventional hot melt adhesive composition of U.S. Pat. No. 4,526,577 (Schmidt et al.), A flat viscosity curve is desirable because the v less with temperature, making the adhesive composition more versatile where viscosity constraints are involved in the application process.

Further, the adhesive composition of the present invention has a lower viscosity than the Schmidt '577 composition. In particular, a comparison between their respective viscosity temperature curves that the adhesive composition of the present invention has a viscosity in the temperature range between 350° F. and 280° F. that is approximately 33% lower than the adhesive composition of the Schmidt '577 patent. A lower viscosity is advantageous in that it enables the adhesive composition to more easily penetrate porous substrates, such as the non-woven materials utilized in disposable diaper. Moreover, a lower viscosity is economically advantageous because it allows the adhesive composition to be applied at lower temperatures. This is a particular advantage in applications where a thinner gauge polyethylene or polypropylene Film is used, since the lower temperature, as a general principle, allows the adhesive to be applied to the thinner polyethylene and polypropylene Films without causing distortion to the Film. No absolute statement about the thickness of the films can be made since the thickness of the films in any application is dependent upon a variety of factors, such as thickness of the glue, retention time etc., all of which are taken into account by those skilled in the art.

In the disposable beverage bottle industry, the PET bottles are subject to a range of temperatures during storage and refrigeration causing expansion and contraction of the bottles. Any glue used on such bottles, whether for labeling or for bottom cup affixation, must have both high and low temperature performance. The Flat viscosity curve and the high tensile strength of the adhesive composition of the present invention makes it particularly suited for the beverage and/or PET bottling industry.

The hot melt pressure sensitive "adhesive composition" of the present invention was compared in Table 1 to the hot melt pressure sensitive adhesive of the prior art (U.S. Pat. No. 4,526,577, Schmidt et al.). In particular, the parameters compared with the following: (1) "tackiness" or inherent stickiness; (2) "elasticity"% elongation at break; and (3) peak tensile strength.

"Tackiness" is determined by means of the Polyken Probe Tack Test. The Polyken Probe Tack Testing Machine provides a means of bringing the tip of a flat probe into contact with these materials at controlled rates, contact pressures, dwell times and subsequently measuring in grams per square centimeter the force required to break the adhesive bond. The probe used had the 280 grit abrasive Finish as recommended by the manufacturer. TMI Testing Machines, Inc., for testing pressure-sensitive adhesives. The contact pressure was 100 gms/cm$^2$, the dwell time was 1 sec., and the rate of test was 1 cm/sec.

"Tensile Strength" is determined by casting the adhesive in a silicone mold several centimeters long with a cross-sectional area of 0.05376 square inches. The casting is then clamped in the jaws of a tensile tester. The jaws are 10 mm apart at the outset of the test, thereby giving an initial length of 10 mm to the adhesive casting. The adhesive is drawn apart at a constant speed of 303 mm/min. while the cell load and the elongation are measured until the break point. From the results peak tensile strength and percent elongation at break are then calculated.

"Elasticity" is then determined by elongating a measured amount of cooled adhesive on a tensile testing machine, till the sample breaks.

"Peak Tensile Strength" is determined by the same method as "Elasticity" but the highest level of force required to elongate the adhesive is of interest.

In Table 1, the "Tackiness" of the adhesive compositions of the Schmidt '577 patent and the present invention are seen as being comparable. However, in regards to "Elasticity," the adhesive composition of the present invention is demonstratively superior, elongating 5150% at break compared to 2554% for the Schmidt '577 adhesive. Moreover, the adhesive composition of the present invention also exhibited superior peak tensile strength, at 70° F., achieving 4.73 lbs. at peak, as compared to 3.36 lbs. for the Schmidt '577 adhesive.

Hence, the oilless hot melt pressure sensitive adhesive composition of the present invention, provides increased strength and elongation over the oil containing hot melt, pressure sensitive adhesive compositions of the prior art without sacrificing either tackiness or viscosity.

Generally, the adhesive composition of the present invention is prepared by blending at about 325° F. 0.1 -1.5 parts by weight anti-oxidant, such as Irganox 1010, 21 -29% by weight of a synthetic polyterpene/petroleum hydrocarbon resin having a R & B softening point of about 10° C. such as Wingtack 10, and 25 to 35% of a high melt point hydrocarbon resin such as Escorez 149-A, having a R & B softening point of about 100 °-110° C. When the above slurry is fluid and at about 300° F, 15 -30 parts by weight of an A-B-A block or A-B-A-B-A-B multi-block copolymer are added such as Stereon 845-A, containing from about 35 -55% by weight Styrene, where polymer blocks A are styrene blocks and polymer blocks B are butadiene or hydrogenated butadiene. When the above mixture becomes smooth, 20 -28% by weight of a synthetic petroleum hydrocarbon resin having a R & B softening point of about 20 ° C., such as Escorez 2520 is added and once again mixed till smooth.

The mixture is blended in a melt at a temperature from about 300° F. -350° F. (134°-162° C.) until a homogenous blend is obtained. The viscosity of the resultant adhesive composition is 675 -725 centipoise (cps) at 380F. as measured by a Brookfield Viscometer.

DESCRIPTION OF THE PREFERRED EMBODIMENT

The following example is given by way of illustration only and should not be construed as limiting the invention in spirit or scope.

EXAMPLE 1

To 25.8 parts by weight of Wingtack 10 (synthetic polyterpene/hydrocarbon resin) was blended 0.60 parts by Irganox 1010 (anti-oxidant and available from Ciba-Geigy) and 30 parts Escorez 149-A, a hydrocarbon resin, at about 325° F. Upon homogeneity of the blend, 19.6 parts by weight of Stereon 845 (copolymer) was added. When the mixture became homogeneous, 24.0 parts by weight Escorez 2520, a synthetic petroleum hydrocarbon resin was added. The resulting hot melt pressure sensitive adhesive composition exhibited a viscosity of 700 cps at 380° F. (Brookfield Thermosel Viscometer).

Overall, the formulation of Example I is summarized as in weight percent as follows:

| | |
|---|---|
| Steron 845-A | 19.60 |
| Escorez 2520 | 24.00 |
| Ecorez 149-A | 30.00 |
| Wingtack 10 | 25.80 |
| Irganox 1010 | 0.60 |
| | 100.00 |

EXAMPLE 2

To 27.9 parts by weight of Hercoflex 500 (a liquid synthetic resinous tackifier available from Hercules, Inc., Wilmington, Del.) was blended with mixing at about 325° F. 0.1 part by weight Irganox 1010 (an antioxidant) and 20 parts by weight of SOLT 168 (a copolymer commercially available from Enichem). Upon homogeneity of the blend, 47 parts by weight of Wingtack 86 (a modified C5 petroleum hydrocarbon resin having an R & B softening point of 88 ° C.), and 5 parts by weight Novotac 101 (a rosin ester having an R & B softening point of 95°-100° C., available from Georgia-Pacific, Atlanta, Ga.), were added. When the mixture again became homogeneous, the resulting hot melt adhesive composition was suited for use. The formulation of Example 2 is summarized in weight percent as follows:

| | |
|---|---|
| SOLT 168 | 20.00 |
| Hercoflex 500 | 27.90 |
| Wingtack 86 | 47.00 |
| Novotac 101 | 5.00 |
| Irganox 1010 | 0.10 |
| | 100.00 |

EXAMPLE

The following example is based upon the availability of an aromatically modified C5 resin having an R & B softening point of about 60° C. To 18 weight percent of Hercoflex 500 is blended with mixing at about 325 ° F. 20 weight percent SOLT 168, and 0.1 weight percent Irganox 1010. When the blend is homogeneous, 60.9 weight percent of the 60° C softening point resin is added. The mixture is again stirred and heated at 325 ° F. until homogeneous. The resultant product is a hot melt adhesive composition that is ready for use. The formulation for Example 3 is summarized below as follows:

| | |
|---|---|
| SOLT 168 | 20.00 |
| Hercoflex 500 | 18.00 |
| 60° C. Softening Point Resin | 60.90 |
| Irganox 1010 | 0.10 |
| | 100.00 |

TABLE 1

| | | COMPOSITION Present Invention | |
|---|---|---|---|
| TEST | Schmidt '577 | Example 1 | Example 2 |
| "Tackiness" Polyken Probe @ 72° F. | 975 gms | 900 gms | 625 gms |
| Total Elongation/ Elasticity "% elongation at Break" | 9.8 in/2591% | 20.6 in/5334% | 19.96/5010% |
| "Peak Tensile Strength" p.s.i. at 72° F. | 3.77 lbs. | 5.31 lbs. | 4.43 lbs. |

I claim:

1. A hot melt pressure sensitive adhesive composition consisting essentially of:
   (a) from about 15% to about 30% by weight of an A-B-A block or A-B-A-B-A-B-multi-block copolymer, wherein polymer blocks A are styrene blocks and polymer blocks B arc butadiene or hydrogenated butadiene and wherein said polymer block A comprises from about 35 to about 55 parts per 100 parts of said copolymer and said polymer blocks B comprise from about 65 to about 45 parts per 100 parts of said copolymer;
   (b) from about 70% to about 85% by weight of one or more compatible tackifying resins having a composite Ring and Ball softening point between about 25° C. to about 50° C.; and
   (c) from about 0.1% to about 1.5% by weight of a stabilizer of the anti-oxidant type.

2. The adhesive composition of claim 1 wherein said composition employs an A-B-A-B-A-B-multi-block copolymer.

3. The adhesive composition of claim 2 wherein said multi-block copolymer contains from about 42 parts to about 52 parts styrene per 100 parts of said copolymer.

4. The adhesive composition of claim 3 wherein said composition employs from about 19 to about 21% by weight of said multi-block copolymer.

5. The adhesive composition of claim 1 wherein said one or more compatible tackifying resins is a composite of three compatible resins selected from the group consisting of (1) a polyterpene resin/petroleum hydrocarbon resin having a Ring and Ball softening point of about 10° C.; (2) a light colored hydrocarbon resin having a Ring and Ball softening point of from 100°–110° C.; and (3) petroleum derived hydrocarbon resins having a Ring and Ball softening point of about 10° C., as determined by ASTM E-28.

6. The adhesive composition of claim 1 wherein from 1 to 3 compatible tackifying resins is employed.

7. The adhesive composition of claim 6 wherein two compatible tackifying resins are employed.

8. The adhesive composition of claim 6 wherein one compatible tackifying resin is employed.

* * * * *

UNITED STATES PATENT AND TRADEMARK OFFICE
CERTIFICATE OF CORRECTION

PATENT NO. : 5,360,854

DATED : November 1, 1994

INVENTOR(S) : FRANK BOZICH, JR.

It is certified that error appears in the above-identified patent and that said Letters Patent is hereby corrected as shown below:

Column 2, line 33, "blocks A arc" should be --blocks A are--.

Column 2, line 51, "adhesive Formulation" should be --adhesive formulation--.

Column 2, lines 53-54, "adhesive Formulation" should be --adhesive formulation--.

Column 3, line 28, "A-B-A-B-A-B" should be --A-B-A-B-A-B---.

Column 4, line 22, "resins have" should be --resins that have--.

Column 4, line 23, "resins) resins to" should be --resins) to--.

Column 4, line 56, "2. a 37 light" should be --2. a "light--.

Column 5, line 1, "hexa[4-(3,5-..." should be --hexa[3-(3,5-...--.

Column 7, line 34, "the v less" should be --the viscosity of the adhesive composition changes less--.

UNITED STATES PATENT AND TRADEMARK OFFICE
CERTIFICATE OF CORRECTION

PATENT NO. : 5,360,854
DATED : November 1, 1994
INVENTOR(S) : FRANK BOZICH, JR.

It is certified that error appears in the above-indentified patent and that said Letters Patent is hereby corrected as shown below:

Column 7, line 41, "curves that the" should be --curves indicates that the--.

Column 7, line 53, "Film is used" should be --film is used--.

Column 7, line 56, "Films without causing distortion to the Film." should be --films without causing distortion to the film.--

Column 7, line 68, "Flat viscosity" should be --flat viscosity--.

Column 8, line 18, "Finish as" should be --finish as--.

Column 10, line 1, "EXAMPLE" should be --EXAMPLE 3--.

Column 10, lines 45-46, "block A comprises" should be --blocks A comprise--.

Column 12, line 5, "of claim 6" should be --of claim 7--.

Signed and Sealed this

Thirty-first Day of October 1995

Attest:

Attesting Officer

BRUCE LEHMAN
Commissioner of Patents and Trademarks